(12) United States Patent
Duric et al.

(10) Patent No.: US 8,542,009 B2
(45) Date of Patent: Sep. 24, 2013

(54) OXYGEN CONCENTRATION MEASUREMENT WITH GMR

(75) Inventors: Haris Duric, Helmond (NL); Josephus Arnoldus Henricus Maria Kahlman, Tilburg (NL); Jeroen Veen, Nijmegen (NL)

(73) Assignee: Koninklijke Philips N. V., Eindhoven (NL)

( * ) Notice: Subject to any disclaimer, the term of this patent is extended or adjusted under 35 U.S.C. 154(b) by 456 days.

(21) Appl. No.: 12/990,986

(22) PCT Filed: May 4, 2009

(86) PCT No.: PCT/IB2009/051824
§ 371 (c)(1),
(2), (4) Date: Nov. 4, 2010

(87) PCT Pub. No.: WO2009/138897
PCT Pub. Date: Nov. 19, 2009

(65) Prior Publication Data
US 2011/0057651 A1    Mar. 10, 2011

Related U.S. Application Data

(60) Provisional application No. 61/053,194, filed on May 14, 2008.

(51) Int. Cl.
*G01R 33/02* (2006.01)
*G01R 33/12* (2006.01)
(52) U.S. Cl.
USPC .......................................... 324/228; 324/252
(58) Field of Classification Search
USPC ................................. 324/228, 252
See application file for complete search history.

(56) References Cited

U.S. PATENT DOCUMENTS

| 4,667,157 | A | 5/1987 | Ciammaichella et al. |
| 5,657,190 | A | 8/1997 | Araki et al. |
| 6,263,722 | B1 | 7/2001 | Fabinski et al. |
| 2004/0170867 | A1 | 9/2004 | Chang et al. |
| 2004/0212933 | A1 | 10/2004 | Kim et al. |
| 2008/0024118 | A1* | 1/2008 | Kahlman et al. .............. 324/204 |

FOREIGN PATENT DOCUMENTS

| EP | 2013893 A | 8/1979 |
| JP | S578442 A | 1/1982 |
| WO | 2005054887 A1 | 6/2005 |

(Continued)

OTHER PUBLICATIONS

Schmid, U., et al.; Theoretical considerations on the design of a miniaturised paramagnetic oxygen sensor; 2006; Sensors and Actuators B (Chemical); 116(1-2)abstract.

*Primary Examiner* — Reena Aurora

(57) ABSTRACT

In an embodiment, an oxygen sensor comprises a giant magnetoresistance device (10), and a magnetic field generator (14, 14a, 14b) arranged to generate a magnetic field (12, 12a, 12b) overlapping the giant magnetoresistance device and an examination region (20). A component ($B_x$) of the magnetic field detected by the giant magnetoresistance device is dependent upon an oxygen concentration in the examination region. In an embodiment, a chip (40) includes one or more electrically conductive traces (14a, 14b) disposed on or in the chip and a giant magnetoresistance device (10) disposed on or in the chip such that electrical current flowing in the trace or traces generates a magnetic field (12a, 12b) that overlaps the magnetic field sensor, said magnetic field being perturbed ($B_x$) by ambient oxygen (24) such that a signal output by the magnetic field sensor indicates ambient oxygen concentration.

11 Claims, 2 Drawing Sheets

(56) References Cited

FOREIGN PATENT DOCUMENTS

| WO | 2005116661 | A1 | 12/2005 |
| WO | 2007042958 | A2 | 4/2007 |
| WO | 2007088502 | A2 | 8/2007 |
| WO | 2007132372 | A1 | 11/2007 |

* cited by examiner

OXYGEN CONCENTRATION MEASUREMENT WITH GMR

CROSS REFERENCE TO RELATED APPLICATIONS

This application claims the benefit of U.S. provisional application Ser. No. 61/053,194 filed May 14, 2008, which is incorporated herein by reference.

The invention relates to the sensor arts, safety arts, medical arts, gas processing arts, and related arts. It finds application in oxygen monitoring in medical settings, various industrial ambient monitoring tasks, and the like.

Oxygen concentration measurement is useful in many clinical settings. In order to improve patient safety, inspired oxygen concentration is routinely measured in anesthesia and critical care medicine. Another example is measurement of inspiratory and expiratory concentrations of oxygen and carbon dioxide to determine patient's metabolic rate. Nonmedical applications of oxygen concentration measurement include industrial and environmental gas measurement and handling tasks.

There are a number of different physical principles described in the literature that can be used to measure oxygen. Electro-chemical, partial pressure, zirconia and paramagnetic responses to oxygen concentration have been contemplated as suitable bases for oxygen concentration measurement. However, existing systems typically exhibit various deficiencies such as slow response time, bulkiness, sensitivity to mechanical vibrations, high cost, or so forth.

A common type of oxygen concentration sensor is a magnetomechanical assembly that includes a dumbbell structure rotatably suspended in a magnetic field, with the "bells" of the dumbbell containing nitrogen or another non-paramagnetic material. If the oxygen concentration rises, it is attracted to the magnetic field due to the paramagnetic nature of oxygen, thus strengthening the magnetic field. The non-paramagnetic bells of the dumbbell are biased out of the strengthening magnetic field, thus producing a deflection of the dumbbell that is related to oxygen concentration. The deflection is detected optically or by another motion detection system. Fabinski et al., U.S. Pat. No. 6,263,722 describes one such dumbbell-based oxygen concentration sensor.

Dumbbell-based oxygen concentration sensors have a mechanical basis of operation, which leads to problematic sensitivity to vibration or other mechanical interference, and makes it difficult to miniaturize the sensor.

The invention provides a new and improved oxygen monitors and oxygen monitoring methods which overcome the above-referenced problems and others.

In accordance with one disclosed aspect, an oxygen sensor is disclosed, comprising one or more magnetic field generators for the generation of a magnetic excitation field in an examination region and Giant Magneto Resistances (GMRs) for the detection of magnetic reaction fields generated by the paramagnetic oxygen molecules within said examination region. The signal (for example, a resistance change) of the GMRs is then indicative of the oxygen concentration in the examination region.

In accordance with another disclosed aspect, an oxygen sensing method is disclosed, comprising: generating a magnetic field within a giant magnetoresistance device and an examination region; perturbing the magnetic field overlapping the giant magnetoresistance device by introducing a concentration of oxygen into the examination region; measuring the perturbation of the magnetic field using the giant magnetoresistance device; and outputting an oxygen concentration value determined based on the measured magnetic field perturbation.

In accordance with another disclosed aspect, an oxygen sensor is disclosed, comprising a chip including (i) one or more electrically conductive traces disposed on or in the chip and (ii) a magnetic field sensor disposed on or in the chip such that electrical current flowing in the one or more electrically conductive traces generates a magnetic field within the magnetic field sensor, said magnetic field being perturbed by oxygen such that a magnetic field detection signal output by the magnetic field sensor is indicative of oxygen concentration.

A detector module may optionally comprise a driver for supplying the at least one conductor with an alternating electrical driving signal. Said driving signal may for example be a sinusoidal voltage or current having a selected frequency. Effects which are induced by said current will then usually be characterized by a corresponding frequency dependence which allows separating them from other effects.

A magnetic sensor device may be provided with a Hall sensor or magneto-resistive elements which may in some embodiments be a GMR (Giant Magneto-Resistance) device, a TMR (Tunnel Magneto Resistance) device, or an AMR (Anisotropic Magneto Resistance) device.

One advantage resides in providing an oxygen sensor with reduced sensitivity to vibration or other mechanical disturbance.

Another advantage resides in providing a compact oxygen sensor.

Another advantage resides in providing an oxygen sensor configured as a chip with no moving parts.

Further advantages of the present invention will be appreciated to those of ordinary skill in the art upon reading and understand the following detailed description.

FIG. 1 diagrammatically shows an oxygen sensor.

Figure 1:
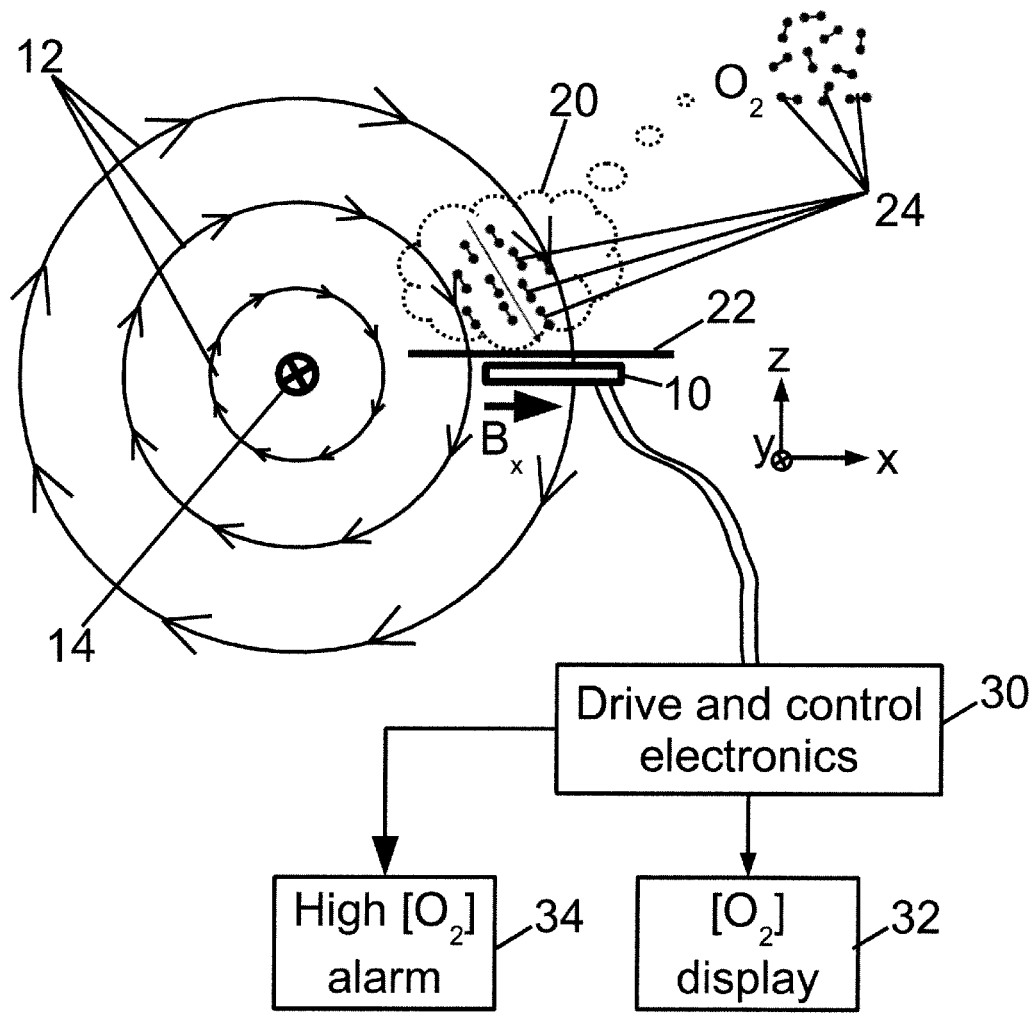

With reference to FIG. 1, an oxygen sensor includes a magnetic field sensor 10 disposed in a magnetic field 12 generated by a magnetic field generator. In FIG. 1, the illustrated magnetic field generator comprises an electrical conductor 14, such as a wire, electrically conductive trace, and so forth. Electrical current flowing in the electrical conductor 14 generates the magnetic field 12 around the electrical conductor 14. FIG. 1 uses a conventional illustrative notation in which the electrical conductor 14 oriented transverse to the plane of the drawing sheet and carrying electrical current flowing "into" the plane of the drawing sheet is indicated by a circle circumscribing an "X" symbol.

The oxygen sensor including the magnetic field sensor 10 and electrical conductor 14 are configured to interact with and measure oxygen concentration in an examination region 20. In the illustrated embodiment, the examination region 20 is defined as a region "above" the magnetic field sensor 10 bounded by an oxygen barrier 22 that prevents oxygen from flowing or diffusing into or "below" the magnetic field sensor 10. In other embodiments, the examination region 20 may be otherwise defined, for example by tubing through which oxygen gas may flow.

Both the magnetic field sensor 10 and the examination region 20 overlap the magnetic field 12. As diagrammatically illustrated in FIG. 1, oxygen molecules 24 each include two oxygen atoms bonded together, thus defining a diatomic $O_2$ molecule having a spatial orientation defined by the O—O bond. Oxygen molecules 24 that are located outside of the magnetic field 12 have random orientation. On the other hand, oxygen molecules 24 located within the magnetic field 12, and of particular interest within the examination region 20, are biased by the magnetic field 12 toward an orientation in which the O—O structures align with the direction of the magnetic field 12. Such alignment is a consequence of the dominant paramagnetic behavior of oxygen molecules 24. It is to be understood that the alignment of the oxygen molecules 24 in the examination region 20 shown in FIG. 1 is diagrammatic—in practice, the magnetic field 12 imposes some bias toward alignment of the oxygen molecules 24 parallel with the magnetic field 12, but the oxygen molecules 24 continue to rotate and translate in accordance with their kinetic energy and only show alignment with the magnetic field 12 in a statistical sense. However, this alignment in a statistical sense is sufficient that the oxygen molecules 24 reinforce and strengthen the magnetic field 12 within the examination region 20.

The magnetic field sensor 10 is generally planar and is viewed "edge-on" in FIG. 1. In the absence of any oxygen concentration in the examination region 20, symmetry of the arrangement of FIG. 1 dictates that the magnetic field 12 is oriented transverse to the generally planar magnetic field sensor 10. In embodiments illustrated herein, the magnetic field sensor 10 is a giant magnetoresistance (GMR) device of the spin-valve type, which is sensitive to the magnetic fields in the x-direction (referencing the Cartesian coordinate system illustrated in FIG. 1) and is insensitive to any magnetic field component oriented transverse to the generally planar GMR sensor 10 (that is, any magnetic field component oriented in the z-direction). In the absence of any oxygen in the examination region 20, the magnetic field 12 is oriented along the z-direction, and so the GMR sensor 10 does not detect any magnetic field.

As oxygen is introduced into the examination region 20 such that the oxygen concentration rises in the examination region 20, the oxygen molecules 24 align (in a statistical sense) with the magnetic field 12 and strengthen the magnetic field 12 in the examination region 20. This perturbation of the magnetic field 12 introduces an asymmetry in the magnetic field that includes a perturbation magnetic field component $B_x$ oriented along the x-direction as diagrammatically shown in FIG. 1. The spin-valve type GMR device 10 detects and measures the perturbation magnetic field component $B_x$ oriented along the x-direction. The measured in-plane component $B_x$ is proportional to, or at least monotonically increasing with, the oxygen concentration $[O_2]$ in the examination region 20.

Suitable drive and control electronics 30 provide power for driving electrical current in the electrical conductor 14 to generate the magnetic field 12, and include detection circuitry for receiving the magnetic field detection signal output by the magnetic field device 10. A suitable output device, such as an illustrated oxygen concentration $[O_2]$ display 32, or an illustrated high oxygen concentration alarm 34, or so forth, provides user-perceptible output indicative of the oxygen concentration, such as a displayed quantitative oxygen concentration value displayed on the $[O_2]$ display 32, an audible warning alarm output by the high oxygen concentration alarm 34 conditional upon the measured oxygen concentration exceeding a safety threshold, or so forth.

The embodiment shown in FIG. 1 is illustrative. Various types of GMR-based devices, as well as non-GMR-based devices, are contemplated as the magnetic field sensor. An example of a non-GMR-based device that can be used as the magnetic field sensor is a Hall effect device. A generally planar Hall effect device is sensitive to the magnetic field transverse to the plane of the device—accordingly, if a Hall effect device is substituted for the GMR device 10 of FIG. 1, it should be rotated 90° so that the unperturbed magnetic field 12 lies parallel with the plane of the Hall effect device and the perturbation magnetic field $B_x$ lies transverse to the plane of the Hall effect device. GMR-based devices generally have an advantage over other magnetic field sensors in terms of sensitivity to the magnetic field. Both GMR-based devices and Hall effect devices are advantageously solid state sensors with no moving parts.

Figure 2:
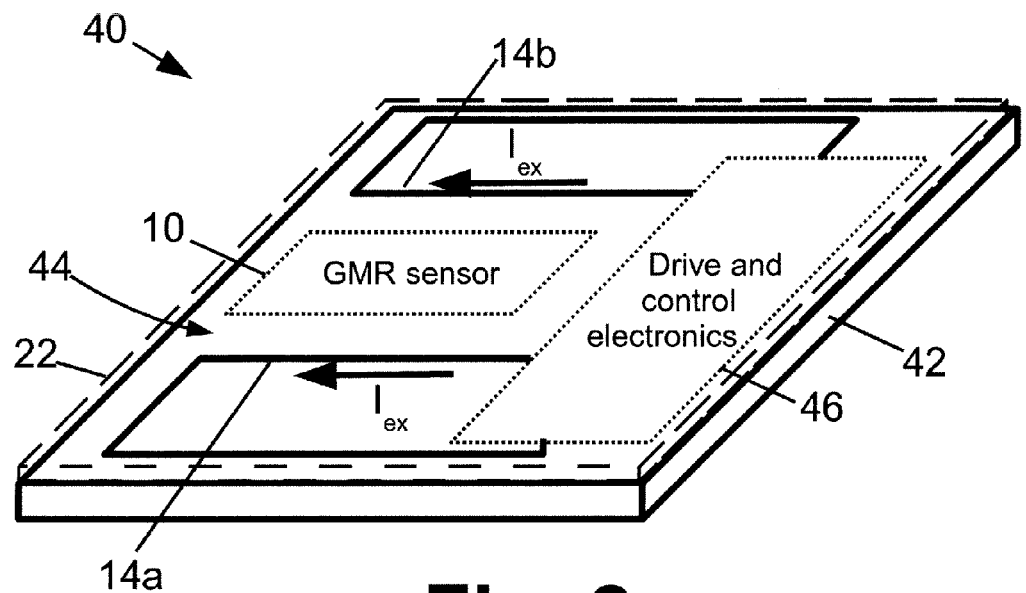
FIG. 2 shows a diagrammatic perspective view of an oxygen sensor configured as a chip.

With reference to FIG. 2, an illustrative oxygen sensor is configured as a chip 40 including a generally planar substrate 42 having a front side 44 supporting the GMR device 10 and one or more electrically conductive traces 14a, 14b that flow a current $I_{ex}$ so as to generate the magnetic field within the GMR device 10. The front side of the generally planar substrate 42 faces the examination region (not shown in FIG. 2), and the generally planar substrate 42 also has a back side (not visible in FIG. 2) facing away from the examination region. In some embodiments, the substrate 42 is a silicon substrate of a type used in silicon-based electronics fabrication, and the GMR device 10 and electrically conductive traces 14a, 14b are formed or fabricated on the silicon substrate 42 using a combination of electronics processing techniques such as: vacuum deposition of metal or metal-containing layers; vacuum or plasma deposition of insulating dielectric layers; photolithographic processing to define deposition windows and/or to laterally selectively remove layers; and so forth. In some embodiments, suitable drive and control electronics 46 are also fabricated on the silicon substrate 42 using silicon electronics fabrication techniques. The on-chip electronics 46 may include some or all of the drive and control electronics 30 shown in the diagrammatic illustration of FIG. 1. The oxygen barrier 22 is suitably formed as a dielectric layer deposited at least over the area of the GMR sensor 10, and optionally deposited over the entire front side 44 of the substrate 42. (The dielectric layer 22 shown in phantom in FIG. 2 blankets the entire front side 44 of the substrate 42). Advantageously, these processing operations may be performed at wafer-level, that is, may be performed on a large silicon wafer having a diameter of a centimeter, or two centimeters, or several centimeters, or larger. Using suitable photolithography masks and the like, an array of dozens, hundreds, thousands, or more of the oxygen sensor component groupings 10, 14a, 14b, 46 can be fabricated at wafer level, followed by a blanket deposition of the barrier dielectric layer 22, followed by dicing of the silicon wafer by sawing, laser cutting, or the like so as to generate dozens, hundreds, thousands, or more of the oxygen sensor chips 40 in a single processing batch.

Figure 3:
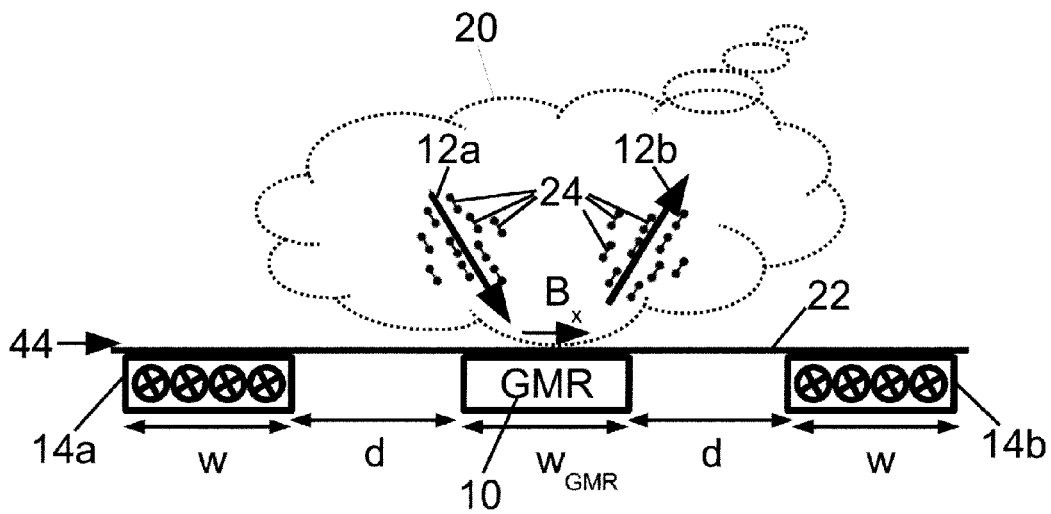
FIG. 3 shows a diagrammatic side view of selected operative components of the oxygen sensor configured as a chip illustrated in FIG. 2.

With continuing reference to FIG. 2 and with further reference to FIG. 3, the oxygen sensor chip 40 illustrated in FIG. 2 has no moving parts. The electrically conductive trace 14a generates a corresponding magnetic field component 12a in the examination region 20, while the electrically conductive trace 14b generates a corresponding magnetic field component 12b in the examination region 20. For both magnetic field components 12a, 12b the influence of oxygen molecules 24 aligning with the magnetic field components 12a, 12b is to enhance the perturbation magnetic field $B_x$ oriented in the x-direction along which the GMR device 10 is sensitive.

In some applications, the oxygen sensor chip 40 is surrounded by an ambient that contains (or may contain) oxygen, such that ambient oxygen (if any) is present at both the front side 44 and the back side of the substrate 42. In this situation, the thicknesses of the dielectric layer 22 and substrate 42 are selected such that component $B_x$ of the magnetic field 12 detected by the giant magnetoresistance device 10 is dependent upon the oxygen concentration in the examination region 20 and is substantially independent of oxygen concentration on the back side of the substrate 42 facing away from the examination region. The oxygen at the front side 44, that is, in the examination region 20, should be substantially closer to the GMR device 10 as compared with any oxygen disposed at the back side of the substrate 42. To accomplish this, the dielectric layer 22 should be as thin as practicable while the substrate 42 should be thick enough that the perturbation of the magnetic field due to any oxygen present at the back side of the substrate 42 is far enough away from the GMR device 10 that such back side oxygen does not substantially alter the magnetic field in the vicinity of the GMR device 10. A silicon substrate thickness of about 300 microns, which is typical for some commercially available electronics-grade silicon wafers, is expected to be sufficient to make the impact of any back side ambient oxygen concentration negligible to the GMR device 10. Optionally, an additional back side barrier (not shown) may be added, such as additional oxygen-impervious plastic laminations adhered to the backside of the substrate to increase the total thickness.

Alternatively, the ambient may be present only over the front side 44 of the substrate 42, with the back side not lying within the ambient. An example of such an arrangement is embedding the oxygen sensor chip 40 in the wall of a container such that the front side 44 is exposed to the contents of the container while the back side is embedded into the container wall. In this arrangement, since only the front side 44 is exposed to any ambient oxygen the substrate thickness is not particularly relevant.

With continuing reference to FIG. 3, as a quantitative example the oxygen sensor chip 40 is considered, with the illustrated spin-type GMR device 10 having width $w_{GMR}$ spaced apart from the electrical conductors 14a, 14b of widths w by distances d, where $w_{GMR}=w=d=3$ microns. In 100 volume-percent $O_2$ the magnetic susceptibility per unit of mass is $\chi_{weight,o}=1.33 \cdot 10^{-6}$ m$^3$/kg. The specific mass is equal to m=1.4 kg/m$^3$, so that the dimension-less $\chi_o=\chi_{weight}$ m=1.87·10$^{-6}$. For the illustrative geometry of FIG. 3 and applying 100% oxygen with an oxygen concentration of one oxygen molecule per cubic micron in the examination region 20 and 25 mW power dissipation, the oxygen sensor chip is expected to generate a signal of about 2.9 nV. The spin valve-type GMR device 10 is expected to exhibit a 1/f noise characteristic where f is the operating frequency, so that improved signal-to-noise ratio (SNR) can be obtained by operating the GMR device 10 in an a.c. mode. In some embodiments the GMR device 10 is operated at a frequency of greater than or about 100 kHz. Assuming current flow in the conductors 14a, 14b of about 100 mA, a white noise spectral density of $e_{th}$=3.5 nV/√Hz and a desired detection signal-to-noise ratio of $SNR_{det}$=10 dB, the detection bandwidth is $$B = \frac{U_{GMR,o}^2}{e_t^2} \cdot 10^{-\frac{SNR_{det}}{10}} = 67 \text{ mHz}$$

and the measurement time is $$T = \frac{1}{2B} = 7 \text{ s}.$$

In such an a.c. mode of operation, the magnetic field detection signal output by the GMR device 10 is suitably demodulated to d.c. and digitized or otherwise processed to obtain an oxygen concentration signal.

The foregoing is merely an illustrative example. In other embodiments, a wider GMR device is contemplated, such as a 100-micron wide device, to provide stronger signal. Similarly, the electrical conductors 14a, 14b can be made wider, or more electrical conductors utilized, in order to carry more electrical current to provide a stronger magnetic field and hence stronger signal. Moreover, while the illustrated embodiments employ an unperturbed magnetic field oriented transverse to the generally planar GMR device 10, other geometries are also contemplated. As an example of another contemplated geometry, the GMR device may be oriented to measure the magnetic field in the z-direction (using the coordinates of FIG. 1) rather than the orthogonal perturbation field $B_x$. In this arrangement the output of the GMR device is never zero, but any change in GMR device output tracks with changes in oxygen concentration. Still further, the magnetic field generator can have a more complex configuration than those illustrated herein, for example including a resistive or superconducting solenoid or electromagnet, a permanent magnet, ferromagnetic materials confining the magnetic flux pathway, or so forth.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An oxygen sensor comprising:
    an oxygen sensor chip including a generally planar giant magnetoresistance device disposed on a generally planar substrate and one or more electrically conductive traces disposed on or in the generally planar substrate and arranged respective to the giant magnetoresistance device such that an electrical current flowing through the one or more electrically conductive traces generates a magnetic field within the giant magnetoresistance device and an examination region, a component of the magnetic field detected by the giant magnetoresistance device being dependent upon an oxygen concentration in the examination region; and
    a detector module operatively coupled with the giant magnetoresistance device and configured to output an oxygen concentration signal based on the component of the magnetic field detected by the giant magnetoresistance device.

2. The oxygen sensor as set forth in claim 1, further comprising:
    an oxygen barrier disposed between the examination region and the giant magnetoresistance device.

3. The oxygen sensor as set forth in claim 1, wherein:
    the generally planar substrate of the oxygen sensor chip has:
        a front side facing the examination region and supporting the giant magnetoresistance device and the one or more electrically conductive traces, and
        a back side facing away from the examination region; and
    a dielectric layer disposed over at least a portion of the front side of the generally planar substrate and substantially blocking oxygen in the examination region from reaching the giant magnetoresistance device.

4. The oxygen sensor as set forth in claim 3, wherein thicknesses of the dielectric layer and substrate are such that the component of the magnetic field detected by the giant magnetoresistance device is dependent upon the oxygen concentration in the examination region and is substantially independent of oxygen concentration on the back side of the substrate facing away from the examination region.

5. The oxygen sensor as set forth in claim 4, wherein the generally planar substrate has thickness of at least about 300 microns.

6. The oxygen sensor as set forth in claim 1, wherein the oxygen sensor is configured as a chip including no moving parts.

7. An oxygen sensing method comprising:
generating a magnetic field within a giant magnetoresistance device and an examination region;
perturbing the magnetic field overlapping the giant magnetoresistance device by introducing a concentration of oxygen into the examination region;
interposing an oxygen barrier between the giant magnetoresistance device and the examination region such that oxygen in the examination region does not reach the giant magnetoresistance device;
measuring the perturbation of the magnetic field using the giant magnetoresistance device; and
outputting an oxygen concentration value determined based on the measured magnetic field perturbation.

8. The oxygen sensing method as set forth in claim 7, wherein the measuring does not include movement of any moving part.

9. The oxygen sensing method as set forth in claim 7, wherein the measuring comprises operating the giant magnetoresistance device at a frequency of greater than or about 100 kilohertz.

10. An oxygen sensor comprising:
a chip including:
(i) two parallel electrically conductive traces disposed on or in a planar front side of the chip,
(ii) a planar giant magnetoresistance device parallel with and disposed on or in the planar front side of the chip and centered between the two parallel electrically conductive traces, and
(iii) an oxygen barrier disposed on the planar front side of the chip and isolating the planar giant magnetoresistance device from ambient oxygen; and
a detector module configured to:
(i) drive electric current through each of the two electrically conductive traces in the same direction such that electrical currents flowing in the two electrically conductive traces cooperatively generate a magnetic field component within and oriented parallel with the planar giant magnetoresistance device, and
(ii) generate an oxygen concentration signal based on the magnetic field component within the magnetic field sensor oriented parallel with the planar giant magnetoresistance device.

11. The oxygen sensor as set forth in claim 10, wherein the detector module is at least partly disposed on or in the planar front side of the chip.

* * * * *